United States Patent [19]
Gingras et al.

[11] Patent Number: 5,925,074
[45] Date of Patent: Jul. 20, 1999

[54] VASCULAR ENDOPROSTHESIS AND METHOD

[75] Inventors: Peter Gingras, Bedford, Mass.; Paul Martakos, Pelham, N.H.; Theodore Karwoski, Hudson, N.H.; Steve A. Herweck, Nashua, N.H.

[73] Assignee: Atrium Medical Corporation, Hudson, N.H.

[21] Appl. No.: 08/759,861

[22] Filed: Dec. 3, 1996

[51] Int. Cl.⁶ ................................................. A61F 2/06
[52] U.S. Cl. ............................. 623/1; 606/191; 606/198
[58] Field of Search ...................... 604/96, 104, 264, 604/280; 606/108, 191, 198; 623/1, 11, 12

[56] References Cited

U.S. PATENT DOCUMENTS

| | | | |
|---|---|---|---|
| Re. 31,618 | 7/1984 | Mano et al. | 3/1.4 |
| 3,105,492 | 10/1963 | Jeckel | 128/334 |
| 3,479,670 | 11/1969 | Medell | 128/334 |
| 3,993,078 | 11/1976 | Bergentz | 128/334 |
| 4,130,904 | 12/1978 | Whalen | 3/1.4 |
| 4,193,138 | 3/1980 | Okita | 3/1.4 |
| 4,208,745 | 6/1980 | Okita | 3/1.4 |
| 4,234,535 | 11/1980 | Okita | 264/519 |
| 4,321,711 | 3/1982 | Mano | 3/1.4 |
| 4,550,447 | 11/1985 | Seiler et al. | 623/1 |
| 4,629,458 | 12/1986 | Pinchuk | 623/1 |
| 4,647,416 | 3/1987 | Seiler et al. | 264/118 |
| 4,731,073 | 3/1988 | Robinson | 623/1 |
| 4,816,339 | 3/1989 | Tu et al. | 428/421 |
| 4,955,899 | 9/1990 | Della Corna et al. | 623/1 |
| 5,028,597 | 7/1991 | Kodama et al. | 514/56 |
| 5,061,276 | 10/1991 | Tu et al. | 623/1 |
| 5,064,593 | 11/1991 | Tamaru et al. | 264/113 |
| 5,123,917 | 6/1992 | Lee | 623/1 |
| 5,152,782 | 10/1992 | Kowligi et al. | 623/1 |
| 5,163,951 | 11/1992 | Pinchuk et al. | 623/1 |
| 5,217,666 | 6/1993 | Tamaru et al. | 264/112 |

(List continued on next page.)

FOREIGN PATENT DOCUMENTS

| | | |
|---|---|---|
| 0233102 | 8/1987 | European Pat. Off. . |
| 0256748 | 2/1988 | European Pat. Off. . |
| 0269449 | 6/1988 | European Pat. Off. . |
| 0605243 | 7/1994 | European Pat. Off. . |
| 2248015 | 5/1975 | France . |
| 3918736 | 12/1990 | Germany . |
| WO95/05132 | 2/1995 | WIPO . |
| WO95/05277 | 2/1995 | WIPO . |
| WO95/05555 | 2/1995 | WIPO . |
| WO96/00103 | 1/1996 | WIPO . |
| WO96/28115 | 9/1996 | WIPO . |

OTHER PUBLICATIONS

Bergeron et al., "Tensile Characteristics of Expanded PTFE for use in Endoluminal Grafting" *Journal of Endovascular Surgery*, vol. 2, 202–203 (1995).

Edelman et al., "Hoop Dreams: Stents Without Restenosis" *Circulation*, vol. 94, No. 6, 1199–1202 (1996).

Diastat Brochure, 3 Pages, Gore Technologies Worldwide.

Marin et al., "Stented Grafts for the Treatment of Arterial Vascular Disease" *Surgical Technology International III*, 421–429.

*Primary Examiner*—C. M. McDermott
*Attorney, Agent, or Firm*—Lahive & Cockfield, LLP

[57] ABSTRACT

A vascular endoprosthesis is formed of a tubular liner preform with a continuous surface and having a diameter smaller than that of an intended vessel. The liner is inserted to a treatment site, and its sheet material undergoes a radially-directed expansion to a final size that fits the vessel. Insertion and in situ expansion are achieved using a catheter assembly in which either an internal stent, such as a stiff-filament helically woven tube, or an inflatable balloon urge the liner preform outwardly against the inner wall of the vessel. The stent, or one or more simple internal snap-rings anchor the expanded liner in place. The expanded liner is porous, or becomes more porous during expansion, and one or more aspects of its porosity are tailored to the intended treatment goal of immobilizing treatment material, isolating cells, or permitting controlled permeation of selected materials.

9 Claims, 3 Drawing Sheets

U.S. PATENT DOCUMENTS

| | | | |
|---|---|---|---|
| 5,225,131 | 7/1993 | Tamaru et al. | 264/113 |
| 5,229,045 | 7/1993 | Soldani | 264/41 |
| 5,234,739 | 8/1993 | Tanaru et al. | 428/131 |
| 5,282,847 | 2/1994 | Trescony et al. | 623/1 |
| 5,282,860 | 2/1994 | Matsuno et al. | 623/12 |
| 5,354,329 | 10/1994 | Whalen | 623/1 |
| 5,389,106 | 2/1995 | Tower | 623/1 |
| 5,413,597 | 5/1995 | Krajicek | 623/1 |
| 5,453,278 | 9/1995 | Chan et al. | 424/422 |
| 5,512,360 | 4/1996 | King | 428/304.4 |
| 5,522,881 | 6/1996 | Lentz | 623/1 |
| 5,527,353 | 6/1996 | Schmitt | 623/1 |
| 5,534,287 | 7/1996 | Lukic | 427/2.25 |
| 5,549,663 | 8/1996 | Cottone, Jr. | 623/1 |
| 5,556,426 | 9/1996 | Popadiuk et al. | 623/1 |
| 5,571,169 | 11/1996 | Plaia et al. | 623/1 |
| 5,571,173 | 11/1996 | Parodi | 623/1 |
| 5,607,478 | 3/1997 | Lentz et al. | 623/12 |
| 5,628,788 | 5/1997 | Pinchuk | 623/1 |
| 5,667,523 | 9/1997 | Bynon et al. | 623/1 |
| 5,674,241 | 10/1997 | Bley et al. | 623/1 |
| 5,683,451 | 11/1997 | Lenker et al. | 623/12 |
| 5,735,892 | 4/1998 | Myers et al. | 606/198 |
| 5,741,324 | 4/1998 | Glastra | 623/1 |
| 5,755,770 | 5/1998 | Ravenscroft | 623/1 |
| 5,755,774 | 5/1998 | Pinchuk | 623/1 |
| 5,769,882 | 6/1998 | Fogarty et al. | 623/1 |

VASCULAR ENDOPROSTHESIS AND METHOD

REFERENCE TO RELATED PATENTS AND PATENT APPLICATIONS

This application relates to the commonly owned United States Patent Applications having the following titles and patent application numbers, which are being filed by applicant of even date herewith: MULTI-STAGE PROSTHESIS, patent application Ser. No. 08/760,113, PROSTHESIS WITH IN-WALL MODULATION, patent application Ser. No. 08/760,115, and EXPANDABLE SHIELDED VESSEL SUPPORT, Attorney patent application Ser. No. 08/759,877. It also relates to applicants'earlier U.S. Pat. No. 5,433,909 and U.S. Pat. No. 5,474,824. The foregoing patents describe methods of making extruded PTFE material having large oriented nodes, uniaxially oriented fibrils and a pore structure of oriented channels that differs at different surfaces, or that varies along the thickness dimension. The aforesaid patent applications each describe constructions or methods of use for prostheses, which are further useful in the embodiments and applications of the present invention. Each of the aforementioned United States Patents and Patent Applications is hereby incorporated by reference herein in its entirety.

BACKGROUND OF THE INVENTION

This invention relates generally to the field of endovascular, thoracic and urological surgery, and relates to catheter balloon delivery stent procedures in particular. Over the last several decades, the treatment of vascular congestion and urological constrictions has been revolutionized by percutaneous balloon angioplasty methods and advances in catheter construction and treatment, which allow a surgeon to insert a simple catheter device along a blood vessel or urethra and surgically shave or mechanically expand the inner wall of the vessel or tubular organ where desired. Such procedures in most instances involve less risk than open surgery, and have proven effective in a wide range of circumstances. However, balloon angioplasty procedures involve some trauma to the vessel wall and this injury may trigger a complex sequence of cellular responses that in many cases lead to restenosis, or closing off, of the treated portion. Studies have reported incidences of restenosis as high as 35–50% following percutaneous transluminal angioplasty of coronary vessels, and incidence of 19–30% after treatment of peripheral lesions. It is therefore an active and major area of medical research to find methods and treatment devices which inhibit or prevent such restenosis.

Uncontrolled cellular proliferation and other factors such as migration of smooth muscle cells into surrounding tissue, and extracellular matrix production by proliferating cells have all been identified as factors which may contribute to the processes of restenosis. Thus, inhibiting any of these three factors may prove effective in preventing the restenosis or short term closing off of a dilated or recanaled vessel following balloon dilation.

The strategies for effecting such inhibition have evolved in three general classes. The first of these is to place a porous, radially expanding metal stent into the affected area to mechanically "hold open" the vessel or tubular organ. Another method involves placing an expandable barrier structure in combination with a stent within the vessel to seal off the inner surface tissue to minimize restenosis. The third strategy involves delivering treatment or medication locally to the affected regions of tissue in the vessel to inhibit stenotic growth processes.

Vascular stents of the first-mentioned class, such as those described and publicized by Palmaz offer good results in mechanically keeping a vessel open for a period of time. However, recent studies have shown that due to the large percentage of open surface or through-openings of these balloon-expanded or self-expanded stents, the same diseased cells which caused the stenotic lesion originally readily proliferate through the open stent structure, causing restenosis of the stented vessel. This process of restenosis has been reported to occur in three stages, or phases, as follows:

| Phase I | Replication of smooth muscle cells (SMCs) |
|---|---|
| 0–3 days | within the medial layer of the vessel |
| Phase II | Migration of SMCs from the medial layer into |
| 3–14 days | the intimal surface |
| Phase III | Proliferation of SMCs within the neointima and from |
| 7 days– | adjoining non-affected areas of the vessel; these cells |
| 1 month | proliferate and grow back into the affected zone |
|  | which has undergone dilation/stent placement |

Various devices have been used or proposed, including porous balloons which are advanced along the vessel to the position of the region to be treated, or hydrogel-coated balloons. Delivery of material to the vessel wall has been enhanced by providing material sandwiched between an inner balloon and an outer porous balloon, so that inflation of the inner balloon ejects medication through the pores of the outer balloon against the vessel lining.

Among purely physical techniques for endoluminal treatment, there have long existed devices such as that shown in U.S. Pat. No. 4,562,596, wherein a thin lining is secured within the vessel to strengthen the wall and prevent aneurysm. Such lining may also act as a barrier against spread of tissue from the covered region of the wall, preventing migration along the vessel or into the bloodstream. Other techniques have been proposed, such as that of the published international application WO9404096 which involves unfurling a reinforced rolled sheet to radially expand it into a shape-retaining tube liner or stent, and that of U.S. Pat. No. 5,316,023 which involves expanding a web-like tubular structure within a vessel. The web-like structure is embedded in an expandable plastic material, which apparently relies on the embedded web for shape retention.

In addition to the foregoing approaches, localized drug delivery has been achieved by periadventitial deposition of an active agent to exploit local diffusion as the primary delivery mechanism. For example, heparin in a matrix material placed in the periadventitial space of arteries following injury has been shown to reduce neointima formation in the first week. Provision of materials in a silastic shell has also been found to be an effective mechanism of drug delivery.

While indwelling vascular liners may prove effective for control of tissue proliferation conditions and restenosis, the implementation of an endoprosthetic liner to be delivered percutaneously poses severe problems due to constraints of size necessary for inserting such a device, and of strength and uniformity necessary to undergo sufficient expansion from a small diameter. While the techniques of catheterization have been developed with much technological detail for the delivery of balloons, for taking of samples, and for the performance of mapping or ablation functions in cardiac tissue, the delivery and installation of a vascular liner would pose unique problems because its operation requires its final diameter to match that of the vessel. An angioplasty balloon is generally formed of highly non-elastic material which is inflated to a high positive pressure to a maximum, fixed, dilated outer diameter. Such balloons are inflated only temporarily to enlarge the stenotic area of the vessel. Pumping balloons for cardiac assistance need not exert such great forces and may be formed with much thinner walls, allowing them to be folded or wrapped to reduce their size and to achieve a small diameter for insertion.

A conventional vascular liner, on the other hand, has a resting state diameter equal to or about ten percent greater than the inner diameter of the vessel in which it is to reside. In order to advance a conventional vascular, graft intraluminally, particularly within small branching vessels to the site of application, it is necessary that it be rolled, folded, or otherwise made much smaller in order to pass through tortuous or disease-affected regions of the vessel.

Accordingly, it would be desirable to provide a vascular liner of enhanced utility to inhibit restenosis and having a small ratio of insertion diameter to expanded diameter.

It is also desirable to provide a vascular liner which is sufficiently compact for intraluminal insertion and installation, yet after insertion and installation maintains a uniform and functional cellular barrier membrane function with dimensional stability and strength.

SUMMARY OF THE INVENTION

These and other features of the invention are achieved in a method of treatment wherein a plastic vessel liner is inserted within a vessel by placement onto an insertion catheter and in an endovascular liner assembly. The catheter is moved into position within the stenotic region under fluoroscopy and the vascular liner is then radially expanded along with an expandable rigidified stent, all in one step to fit an affected site in the vessel or tubular organ. The small OD tubular liner has a hollow center lumen sufficiently large to house a radial expanding stent and inflation balloon, and has a generally cylindrical shape and a length equal to a selected treatment interval along the vessel. Its initial or resting state diameter is substantially less than the inner diameter of the vessel in which it is to be inserted. Once inserted to the desired site within a vessel, the liner is deformed by expanding it beyond its limit of plastic deformation to enlarge the liner. This simultaneously develops or enhances porosity in the liner which, as discussed further below, may be tailored in any of several ways to achieve a desired set of controlled tissue growth, controlled material delivery or controlled growth inhibition characteristics. Once fixed in place by the expanded inner stent, the insertion catheter is then withdrawn, leaving the expanded liner fitted in position on the outside of the stent within the vessel. The liner may be expanded using a radially expandable stent, such as a porous stainless steel tube of Palmaz type, or using a helical or crossed-helical wire mesh stent that expands radially. Alternatively, an angioplasty balloon or specially shaped balloon may be fitted within the liner and may simply be inflated to stretch the liner and alter its size and porosity. In this case, a separate stent or anchor ring may be provided as a secondary step to secure at least one end of the expanded liner after the balloon is withdrawn.

Preferably the liner on the outside of the stent is made of a polytetrafluoroethylene (PTFE) or similar fluoropolymer, which most preferably is formed in a tubular shape by extrusion at high pressure of a paste consisting of powder material with a lubricant or extrusion aid, such as Isopar or other mineral spirit. Following extrusion, the tube may be stretched in a direction along its axis, by a factor of between approximately 2 and 10 to develop a microporous structure consisting of circumferentially-extending nodes, or solid fragments with radially-extending interstitial spaces between the nodes. The interstitial spaces are filled with a multitude of thin connective fibrils, which allow relatively unhindered fluid and gas communication radially through the wall of the liner. Preferably the PTFE material has a nodal structure in which relatively large nodes extending 100 to 1000 micrometers in a radial direction, and most preferably extending between 200–500 micrometers radially, and extending 100–1000 micrometers or more in a circumferential direction is used, as described for example in the aforesaid commonly owned U.S. patents which are hereby incorporated by reference. This large nodal structure enables the liner to stretch by a factor of 5 to 10 times without membrane rupture. This axially-stretched PTFE material has negligible Poisson coupling, so that when the liner is expanded radially, the forces in the axial and circumferential directions of the sheet do not couple very strongly, and it does not shorten by any appreciable amount in length, while it may be expanded by a factor of two or more in radius. This radial expansion of the liner does result in a slight thinning of its wall, in addition to radial stretching of the circumferentially oriented nodal structure of the PTFE material therein. The expanded liner thus maintains a nearly equivalent pore structure to that originally possessed by the unexpanded liner.

After balloon/stent expansion, the angioplasty balloon (if the expansion has been performed by balloon) is deflated and withdrawn, leaving the expanded liner in place, supported by an internal expanded stent or support. A plastic or wire snap expansion ring or similar stent device may be placed as a secondary step to internally secure the liner at both its upstream end and downstream ends tightly against the inner surface of the diseased vessel wall as an alternative to a one-step balloon/stent insertion technique. Preferably, a fully supporting stent is used, to prevent leakage and accumulation of fluid between the liner and the vessel wall. Also, a vessel liner can be placed onto an expandable stent as a one-piece assembly by which a balloon catheter dictates or expands both the sent and liner simultaneously, and the catheter may be disengaged or deflated leaving the stent and liner to remain fixed in place securely against the vessel wall after the delivery catheter has been withdrawn.

BRIEF DESCRIPTION OF THE DRAWINGS

These and other features of the invention will be understood with reference to the drawings of the illustrative embodiments taken together with a description thereof, wherein.

DETAILED DESCRIPTION

Figure 1:
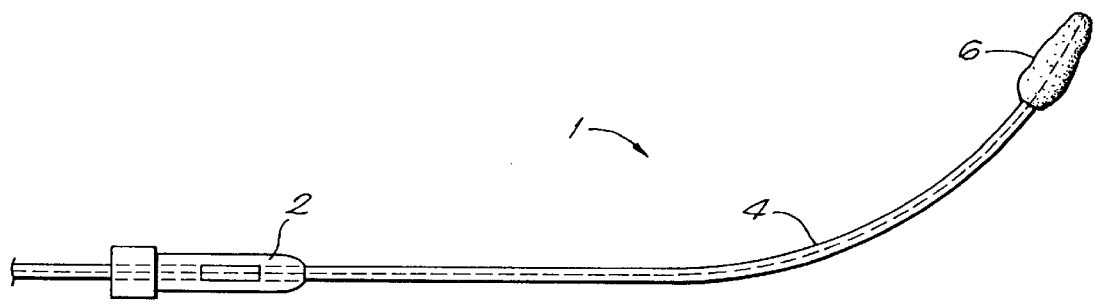
FIG. 1 illustrates a prior art angioplasty balloon for treating vascular restenosis.

A brief discussion of the prior art will clarify the nature of the problem addressed by the present invention, as well as certain conventional aspects of catheter devices which are assumed known for purposes of practicing the invention. FIG. 1A illustrates generally a prior art catheterization device 1, which illustratively may be a simple angioplasty balloon assembly, having a handle 2 which resides outside the body, a long tubular member 4 which extends from the handle and is advanced within a vessel to a treatment site, and a tip assembly 6. In the case of an angioplasty balloon, the tip assembly may simply consist of an inflatable balloon. More generally, the tubular body 4 may include two or more tubes defining an inner lumen and an outer lumen which may be used for inflating the balloon and for sampling fluids or tissue ahead of the tip, respectively. The assembly 6 may include, rather than a simple balloon, various forms of treatment or diagnostic device, such as an endoscopic viewer, a laser, rf, cryogenic or other treatment instrument, or a mechanism for medicating or sampling tissue in the region of the tip. Among known constructions for balloon pumping assemblies, it is common to have one or more inextensible and even torsionally stiff wires running the length of the catheter body 4 for applying turning or wiggling forces to the tip region. In general these catheter devices are inserted by first inserting a thin, flexible and steerable guide wire, and then passing the catheter or balloon over the guide wire to a desired location.

Without extensive discussion in the description which follows, it will be assumed for purposes of example, that the catheter body employed for the present invention involves a simple single or double lumen, one or two tube, catheter construction with some auxiliary mechanism, such as a wire or cable for effecting a push-pull motion at the tip of the catheter. A great many mechanisms for affecting such capabilities are known in the art and may be substituted for the described elements wherever appropriate.

Figure 2:
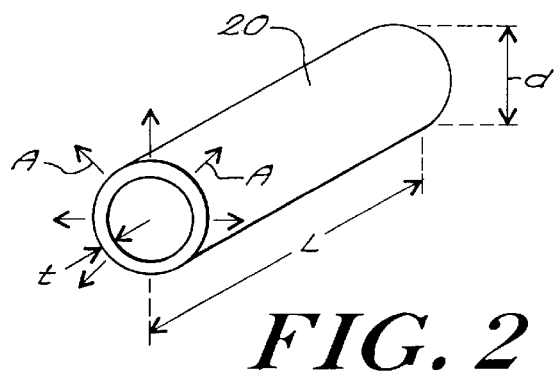
FIG. 2 shows a vascular liner before installation in accordance with the present invention.

It will be appreciated that for insertion to a site such as a human aorta having an inner diameter of 14 to 30 millimeters, the site being normally accessed percutaneously via the femoral artery, a structure capable of having a final dimension which is large compound to the diameter of the vessel within which it is inserted for passage to its target site. The dimensional constraints imposed for this manner of access by the vascular route are specifically addressed in accordance with applicant's invention by providing a liner blank or preform 20 as shown in FIG. 2 having a roughly cylindrical shape like a slice of short tubing, and having an external diameter d substantially less than the lumenal diameter of the vessel. The tube is intended for fitting within a vessel having an internal diameter of between approximately 1.5d and 3d or greater. As illustrated, the wall thickness t of the tube 20 is relatively large in proportion to its diameter, e.g., a thickness of 0.5 to 3.0 millimeters for a tube which may, for example, be only 4 to 10 millimeters diameter. A typical length L for treating a stenotic vessel site would be two to eight centimeters long. The foregoing measurements are illustrative only. It will be understood that the important dimension for this aspect of the invention is that the tube diameter d is of smaller size than the vessel in which it is to be fitted, and has a preselected length L established by the surgeon in relation to the length of the passage which is to be repaired.

Figure 3:
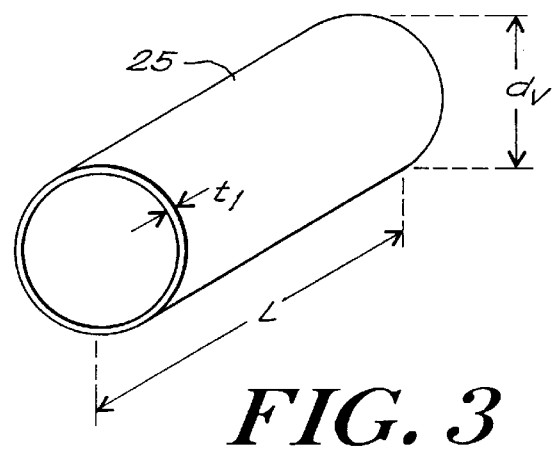
FIG. 3 shows the vascular liner of FIG. 2 after installation.

In accordance with a principal aspect of the present invention, the liner tube 20 is inserted up to a locus within a vessel and is then installed by radially expanding it, as indicated by the arrows A of FIG. 2, to produce an expanded liner 25 of full length as shown in FIG. 3 in which the wall material has been radially stretched in situ. Liner 25 has a larger diameter $d_v$ substantially equal to that of the vessel in which it has been expanded, and correspondingly its wall thickness $t_l$ becomes thinner than the thickness t of the preform, having undergone a thinning due to the radial expansion. Its length L, on the other hand, remains essentially unchanged. The reasons for change in thickness, but not length, upon expansion, are related to the peculiar microstructure introduced in PTFE when it is expanded or stretched and sintered. Briefly, because stretching introduces a node-and-fibril structure in PTFE, stresses along one dimension have negligible Poisson coupling into the directions which are not stretched.

In expanded PTFE, the stretching fractures the solid material, leaving a fairly regular array of globs of solid material, referred to as nodes, which are interconnected to each other by a multitude of thin fibrils extending between the nodes and aligned more or less parallel to the axis or axes of stretch. In the case of radial expansion of the liner, the expansive process might be expected to introduce a node structure into the PTFE material, such that the liner has nodes with fibrils filling in between the nodes and the fibrils aligned circumferentially about the tube. These nodes would not extend for any great dimension along a circumferential contour, but be fractured, resulting in a porosity extending in fibril-filled channels between nodes through the wall of the tube. This mechanism of the plastic material fracturing but remaining connected by a fibril is typical of PTFE. In practice, however, with the aforesaid large circumferentially-extending nodes interconnected by axially-extending fibrils, the relatively large amount of PTFE material in each node and the fact that the liner is pressed radially inward by the surrounding vessel as the liner is expanded may allow the liner to increase its radial dimension when the balloon is inflated, while maintaining its large circumferential node structure as a porous solid upon expansion resulting in very little Poisson coupling between the different directions of stretch. As a result, the length L of the tube remains substantially constant during radial expansion while the diameter of the tube may be increased by a factor of ten or more and the wall thickness may decreases by an amount which corresponds to, but is not strictly proportional to the amount of radial expansion. Thus, the "as-expanded" length is substantially the same as the starting length-before radial expansion is performed.

Figure 2A:
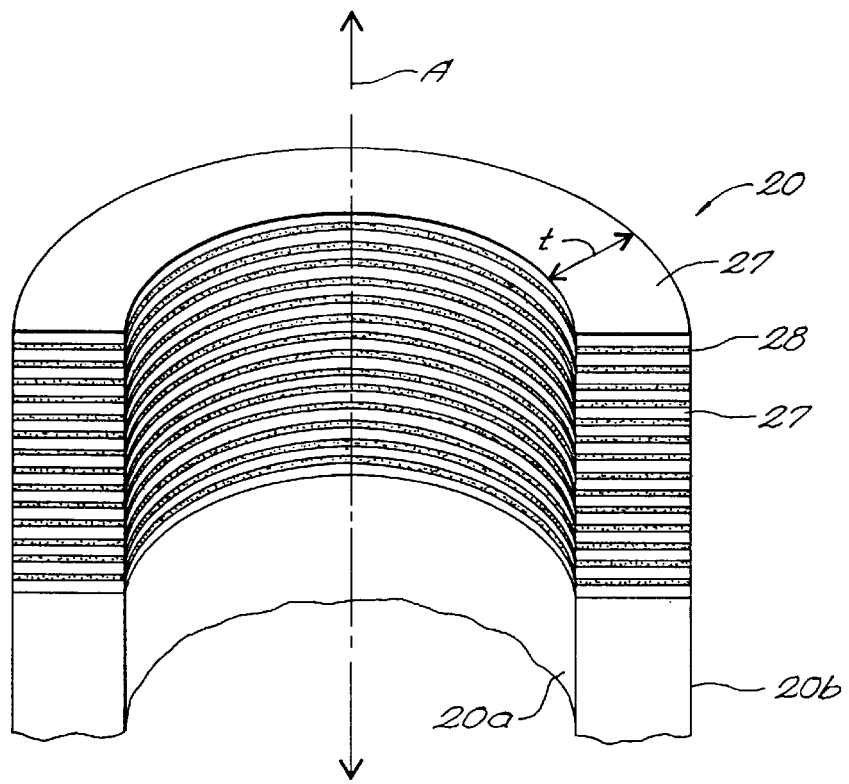
FIGS. 2A and 3A illustrate tailoring of porous microstructure in the continuous vascular liner of FIGS. 2 and 3.
Figure 3A:
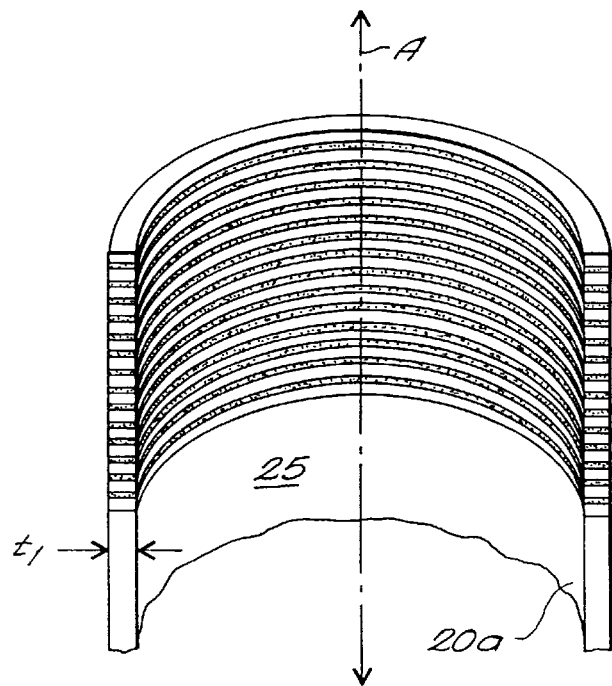

FIGS. 2A and 3A are schematic representations of the node structure in the PTFE material of an axially-stretched embodiment of the liner 20 and a radially expanded liner 25, respectively made from the liner 20. As illustrated in FIG. 2A, the liner 20 prior to use preferably has a porous microstructure wherein nodes consist of relatively large circumferentially extending plates 27, and the fibrils 28 extend in an axial direction along the tube axis "A" between plates. This structure results in mechanical properties like those of a child's "slinky" toy, and corresponding to its "slinky-like" geometry, the tube is relatively crush-proof as regards radial pressure and is relatively springy and flexible along its axial direction. The mechanical strength given by the flat washer-like aspect of the nodes 27 is useful for withstanding stresses involved in insertion along the vessel. In addition, the nodes provide a high mass of plastic material, distributed in a narrow band about the circumference so that it may undergo a relatively high degree of purely radial expansion without excessive thinning or rupture of the wall. Preferably, the nodes provide a mass reservoir of PTFE material greater than fifty weight percent of liner 20 to allow dependable radial expansion of the liner without rupture of the liner wall. Furthermore, the nodes 27 are essentially solid plates, with axially adjacent plates defining channels through the fibril-packed interstices that communicate between the inside 20a and the outside 20b of the tube. This orientation allows a fairly direct control of porosity across the wall by controlling the initial rate and amount of axial stretching. It should be noted, however, that FIG. 2A is a schematic representation and the form of the nodes has been idealized. In practice, the preferred nodes may extend entirely through the tube wall, but may be limited in overall extent to a width between one quarter and several millimeters, rather than forming complete annular rings around the tube.

This structure is described in detail in U.S. Pat. No. 5,433,909, assigned to the Assignee of the present invention.

FIG. 3A schematically shows the node structure of an axially-stretch PTFE liner 20. With the aforesaid node structure of substantially parallel annular plate-like segments, when the balloon radially expands the liner against the pressure of a stenotic vessel wall, the node structure will thin slightly but remain substantially the same. With radial expansion, a mass reservoir of material which can deform without rupture, enlarging its circumferential dimension while still preserving a flat nodal body and general orientation transverse to the fibrils. In this case, each of the relatively large flat nodes 27 oriented perpendicular to the axis and extending circumferentially about the center still retains the washer-like mechanical strength of the original liner and its pore/channel orientation. That is, the entire thin membrane expands as a fairly uniform arrangement of nodes interconnected by fibrils that extend from each node to adjoining nodes, and the nodes therefore continue to extend entirely through the wall or have a regular reticulated spacing.

It should be repeated here that the liner is preferably made by extrusion from a paste under high pressure as described in applicant's aforesaid U.S. Pat. No. 5,433,909, to which reference is made for a full description of representative paste extrusion techniques. Extrusion of tubes at high pressure forces the long molecules in the flowing resin to both assume a high degree of mutual alignment, and to come into close proximity with each other such that Van der Waals-type forces are active and the molecules bond fairly strongly to each other. As a result, subsequent stretching, as described above, introduces a fairly homogeneous and strong node and fibril microstructure into the finished product. As described more fully below, the practice of the present invention does not require the extremes of tensile strength necessary for a vascular graft, but instead requires a level of homogeneity and material strength that permits stretching without developing weak spots or rupturing. Accordingly, the material of the present invention may be made with higher levels of lubricant and using PTFE powders having a lower molecular weight distribution than indicated for the more exacting applications described in the aforesaid patent applications. That is, the PTFE tubes, while made by extrusion, are compounded for stretchability rather than tensile strength.

In accordance with the method of the present invention, the liner is radially expanded as it sits within a blood vessel, generally to an enlarged size no more than about 15–20% larger than the nominal vessel diameter to assume the approximate internal diameter of the adjacent non-stenotic vessel.

Figure 4A:
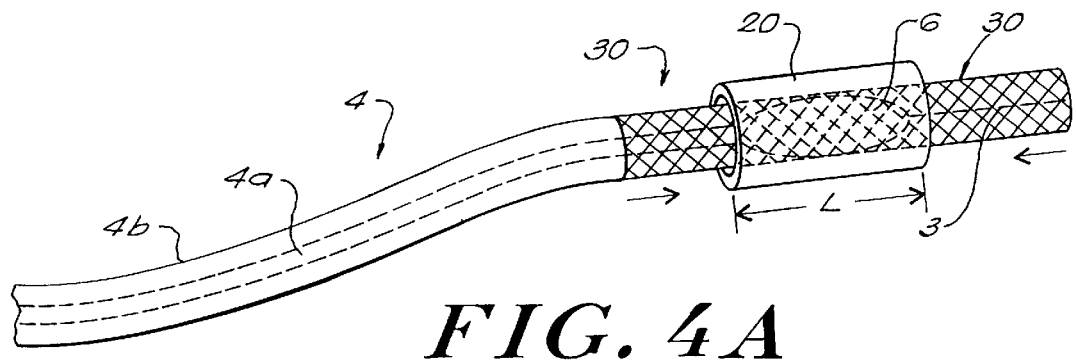
FIGS. 4A and 4B show a preferred installation device and the installed vascular liner of FIG. 2.
Figure 4B:
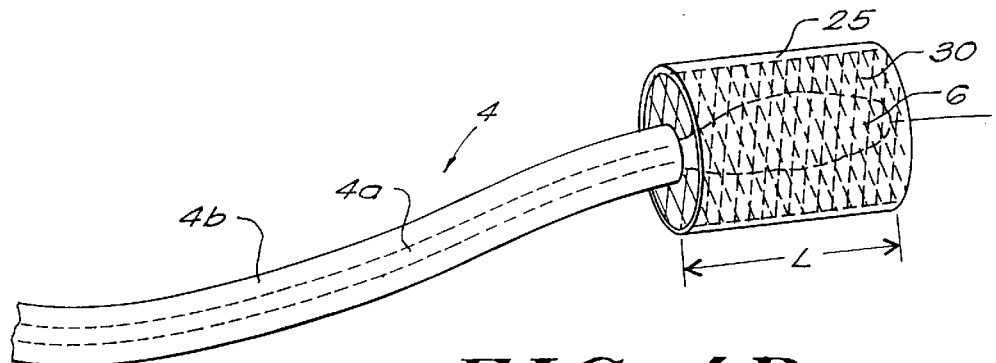

FIGS. 4A and 4B illustrate mechanisms employed for radially expanding the preform 20. FIG. 4A is a view showing different elements variously arranged in successive layers of the apparatus, while FIG. 4B shows the assembled device during an installation procedure. As shown in FIG. 4A, a balloon catheter assembly 4,6 provides the basic installation tool for the package. A wire or plastic stent 30 is placed around the balloon 6, the stent 30 being formed with thin stiff filaments disposed in two or more opposed helices, so that it is free to move outwardly as it is expanded by balloon 6, thereby also shortening its length and bringing one end toward the other. With this construction, the diameter of the stent may be made to increase dramatically, since the stent 30 may be quite long and may readily permit a length-dimension change ΔL of one to three inches, which, because of the stiff helical windings, results in a change in radius that is inversely proportional to the number of windings in one helix. The liner 20 is placed over the wire stent 30. As shown in FIG. 4A, the balloon 6 is inflated via an internal tube 4a, while the stent has its ends constrained between the external tube 4b of the catheter assembly at its proximal end, and a central guide wire or actuation wire 3 at its distal end.

Figure 5:
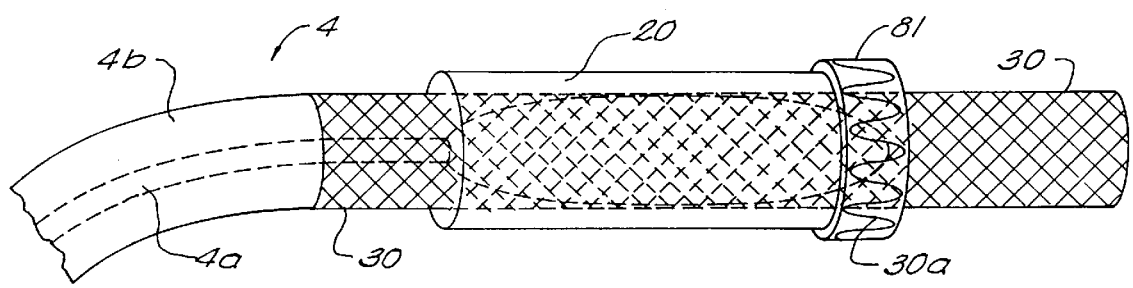
FIG. 5 illustrates an anchor ring enclosed within a two-layer sheath formed by folding the vascular liner of the present invention.

Operation of the device of FIGS. 4A, 4B is as follows. The balloon catheter is inserted by the usual fluoroscopic or ultrasound balloon angioplasty insertion techniques to the site of a vascular lesion, treated stenosis or the like, and with the liner axially centered at the site to cover the entire affected stenotic lesion, the balloon is inflated to simultaneously urge both the stent and liner uniformly radially outward. The expanded stent and liner are left in place, while the angioplasty balloon catheter is deflated and withdrawn. In further refinements or variations of the basic mechanism, the stent structure, as noted above, may be replaced with one or more simple circular rings to anchor the expanded liner firmly against the vessel wall, and the invention also contemplates that the liner may be expanded solely by longitudinal contraction of the helical stent, without reliance on a balloon. In that case the pull-wire 3 is provided within the catheter lumen, or the inner and outer telescoping tubes 4a, 4b are arranged, to vary the stent length and thereby enlarge its diameter for expansion of the cylindrical liner. Furthermore, the stent may be located outside the liner, with one or more internal rings to fix the liner within the stent once it has expanded. However, in view of the risks of tearing of the liner during expansion, use of internal stent is preferred to having the liner positioned inside the stent. If a circular anchor ring 30a is used to secure the expanded liner against the wall of the vessel, the anchor ring can be enclosed within a two layer sheath 31 formed by folding the liner 20 back over itself, as illustrated in FIG. 5. This sheath structure, as well as a method of forming the sheath, is described in detail in U.S. patent application Ser. No. 08/759,877, referred to above and assigned to the Assignee of the present invention.

In accordance with a further feature of the invention, applicant contemplates the use of specially configured balloon structures which include a laser, RF or other energy treatment applicator. In this case, the liner and stent structure are preferably initially located ahead of (or behind) the balloon. The balloon performs a conventional angioplasty procedure, applying treatment energy and/or pressure to the vessel wall, after which the liner is drawn back (or advanced) over the balloon and is expanded at the treatment site as previously described.

As noted above, the liner is preferably made of a PTFE material, which has the property that, upon expansion, it changes from a continuous sheet to a sheet which on a microscopic level is formed of small nodes or nodal bodies interconnected by myriad thin fibrils, thus imparting a selectively permeable or microporous structure to the sheet material. One consequence of this stretch-fracturing of the material is the decoupling of axial and radial dimensional interdependence. That is, unlike a cylindrical tube formed of a bias-woven textile or of a conventional plastic or solid with high tensile strength, changes in length do not directly result in changes of diameter, and vice versa. That is, the PTFE tube has little or no Poisson coupling. This property allows the surgeon to select a length of liner to cover the lesion, without having to account for any decrease in length occurring after radial expansion. A second beneficial aspect of this factoring into a node-and-fibril microstructure, which applicant employs to advantage, is the ability to tailor the porous microstructure to achieve different specific biological effects, as follows.

It has been long realized that the thin flexible fibrils of PTFE can be bent aside or displaced by growing cells, and that this property allows a certain degree of natural tissue regeneration to occur on an implanted PTFE prosthesis. This fibril structure allows cells to be anchored and immobilized in the PTFE pores in much the same way as in natural tissue, and it allows them to continue to grow, provided the fibrils are not too short, i.e., are not under about five microns long, corresponding generally to a pore size of one or two microns. It has also been recognized that such PTFE may have a pore size to be highly gas-permeable, and may be fabricated to be selectively permeable to diffusion of fluids or small molecules. In the prior art, PTFE has accordingly found uses in diverse applications such as non-stick breathable wound dressing and implantable vessel grafts by a suitable tailoring of the porosity. In addition, as discussed in commonly-assigned U.S. Pat. No. 5,433,909 the fibril and node orientation may be controlled to provide an anisotropic or directional porosity.

It is applicant's understanding that many of the mechanisms of restenosis remain to be clearly elucidated and may involve vessel wall surface chemistry and free cytokines, processes mediated by circulating cells, or processes mediated by purely physical adhesion, clotting or accretion mechanisms. In accordance with a further aspect of the present invention, applicant forms a liner wherein a pore structure is adapted to either enhance or inhibit one or more of these mechanisms.

For example, by arranging to stretch an extruded tube of PTFE by an amount to introduce pores of 2, 10, 50 or 100 micrometers, and forming the liner preform of the stretched porous material, once expanded in the vessel, will be either relatively impermeable to cells (for porosity under two micrometers), or will allow the slow penetration and growth of cellular tissue (for porosities of 5 to about 50 micrometers), or will be quite porous (for much larger porosities). Similarly, if one were to start with a tube of porous material which had been drawn through a die or calendared to orient the nodes at its outer surface like flattened scales, the subsequent radial expansion within the vessel by a factor of two or so would preserve some of this node shape and orientation and result in somewhat contorted or obstructed porous pathways between inner and outer surfaces of the tube. Depending on node size of the starting PTFE material (before in situ expansion), this node orientation will be effective to further reduce the rate of fluid diffusion to the vessel wall, to block cellular diffusion, or to block large molecule diffusion, and thus will alter the surface chemistry or biological environment of the vessel wall. In like manner, a straight axial stretching of an extruded PTFE tube may be used to form washer-like nodes with through-pore spaces that assure ready fluid communication directly through the wall, and the extent of this initial stretching of the material and the subsequent in situ radial expansion may each be controlled to provide a porosity in the liner that is fine enough to prevent shedding of cells from the vessel into the bloodstream, or prevent migration of cells from the bloodstream to the underlying surface. Thus, the liner may be formed of a material which either has, or acquires upon in situ expansion, a level of porosity that is selected to either (1) allow movement of cells through the liner wall, (2) allow movement of fluids and gases through the liner wall but prevent movement of cells therethrough, (3) further prevent movement of large molecules, or (4) prevent movement or growth of cells, but allow permeation of gases and small molecule fluids or solutions through the liner wall.

Thus, in accordance with one aspect of a method of treatment according to the present invention, the starting and final porosities of an in situ expanded liner will be selected to treat a specific cellular proliferation condition. For example, an endothelial tumor may be substantially completely isolated by employing a liner with porosity below two micrometers, whereas a non-proliferative or non-metastasizing lesion may be structurally strengthened by a 5–50 micrometer liner that enhances and defines areas of tissue reconstruction. For simple stenoses, the appropriate porosity will be apparent once the physical mechanisms of restenosis have been more firmly established. What is important is that the present invention permits both selection and tailoring of the liner porosity, in addition to providing for insertion of an initially small liner that expands to a continuous cylinder within the vessel.

In addition to PTFE, other materials having suitable biocompatibility properties may be used to form liners for in situ expansion. Such materials include olefin-derived materials commonly used for vascular grafts, or acrylic polymers. Hybrid materials made by the addition of small amounts of such materials or of elastomeric material to a PTFE blend is expected to provide improved stretch characteristics simultaneously with porosity and strength in the stretched liner. However, neither the pore-forming properties nor the decoupled Poisson characteristics which are present in PTFE are believed to be achievable in such favorable form in these other materials when used alone, and for this reason the preferred material for applicant's in situ expanded vascular liner is a seamless expanded PTFE or similar fluoropolymer tube material.

The invention being thus described, variations and modifications will occur to those skilled in the art, and all such variations and modifications are considered to form part of the present invention, within the scope of the claims appended hereto.

What is claimed is:

1. An endovascular liner assembly comprising
   a tube of porous expanded fluoropolymer having a microstructure of nodes and fibrils, the tube with negligible Poisson coupling, and
   a radial expansion element positionable within the tube for selectively enlarging the diameter of the tube without significantly changing the length of the tube.

2. The endovascular liner of claim 1, wherein the radial expansion element is a balloon.

3. The endovascular liner of claim 1, wherein the radial expansion element is a stent.

4. The endovascular liner of claim 1, wherein the fluoropolymer is PTFE.

5. The endovascular liner of claim 1, wherein a substantial plurality of the nodes are circumferentially-oriented and extend for a distance greater than 100 micrometers in a circumferential direction around the tube.

6. An endovascular liner assembly comprising a tube of porous expanded PTFE having a microstructure of nodes and fibrils, a substantial plurality of the nodes being circumferentially-oriented nodes extending for a distance greater than 100 micrometers in a circumferential direction around the tube, and a radially expandable stent within the tube being adapted for balloon expansion said nodes providing a mass reservoir of PTFE greater than fifty weight percent of said tube as an expandable plastic body so that expansion dependably enlarges the radius of said tube without rupture.

7. An endovascular liner assembly comprising a tube of porous expanded PTFE having a microstructure of nodes and fibrils, a substantial plurality of the nodes being circumferentially-oriented nodes extending for a distance greater than 100 micrometers in a circumferential direction around the tube, and a radially expandable stent within the tube, said nodes providing a mass reservoir of PTFE greater than fifty weight percent of said tube as an expandable plastic body so that expansion dependably enlarges the radius of said tube without rupture.

8. An endovascular liner assembly comprising a tube of porous expanded PTFE having a microstructure of nodes and fibrils, a substantial plurality of the nodes being circumferentially-oriented nodes extending for a distance greater than 100 micrometers in a circumferential direction around the tube.

a two layer sheath formed by folding said tube back over itself, said sheath being closed at one end, means at said end for securing said sheath within a vessel, and a radially expandable stent within the tube being adapted for balloon expansion, said nodes providing a mass reservoir of PTFE greater than fifty weight percent of said tube as an expandable plastic body so that expansion dependably enlarges the radius of said tube without rupture.

9. An endovascular liner assembly comprising a tube of porous expanded PTFE having a microstructure of nodes and fibrils, a substantial plurality of the nodes being circumferentially-oriented nodes extending for a distance greater than 100 micrometers in a circumferential direction around the tube, and a radially expandable balloon within the tube adapted to inflate the tube, said nodes providing a mass reservoir of PTFE greater than fifty weight percent of said tube as an expandable plastic body so that expansion dependably enlarges the raduis of said tube without rupture.

* * * * *

UNITED STATES PATENT AND TRADEMARK OFFICE
CERTIFICATE OF CORRECTION

PATENT NO. : 5,925,074
DATED : July 20, 1999
INVENTOR(S) : Peter Gingras et al.

It is certified that error appears in the above-identified patent and that said Letters Patent is hereby corrected as shown below:

<u>Title page,</u>
Item [75], Inventors, please delete "Hudson" and insert -- Hollis --;

<u>Column 10,</u>
Line 53, after "fibrils,", insert -- the nodes having a mass sufficient to provide --;

<u>Column 12,</u>
Line 2, after "tube" delete the period ".", and insert a comma -- , --.

Signed and Sealed this

Twenty-first Day of October, 2003

JAMES E. ROGAN
*Director of the United States Patent and Trademark Office*